United States Patent [19]

Shuttleworth et al.

[11] Patent Number: 5,248,816
[45] Date of Patent: Sep. 28, 1993

[54] PROCESS FOR MAKING 2-HYDROXYMANDELIC ACID AND 2-HYDROXYBENZALDEHYDES

[75] Inventors: Ralph Shuttleworth, Stevenston, Scotland; Jan M. Fielden, Bury; Daniel Levin, Manchester, both of England

[73] Assignee: Imperial Chemical Industries PLC, London, England

[21] Appl. No.: 958,058

[22] Filed: Oct. 8, 1992

[30] Foreign Application Priority Data

Oct. 11, 1991 [GB] United Kingdom ............... 9121656

[51] Int. Cl.$^5$ ...................... C07C 59/48; C07C 45/00
[52] U.S. Cl. ................................ 562/470; 568/432; 568/435
[58] Field of Search ................. 562/470; 568/432, 435

[56] References Cited

U.S. PATENT DOCUMENTS

| | | | |
|---|---|---|---|
| 3,867,434 | 2/1975 | Diamond | 562/470 |
| 3,954,808 | 5/1976 | Elliott et al. | 562/470 |
| 4,163,759 | 8/1979 | Bauer et al. | 260/600 |
| 4,339,602 | 7/1982 | Schouteeten et al. | 562/466 |
| 4,855,323 | 8/1989 | Wess et al. | 562/470 |
| 5,004,754 | 4/1991 | Fortin, Jr. et al. | 562/470 |

FOREIGN PATENT DOCUMENTS

| | | |
|---|---|---|
| 023459 | 2/1981 | European Pat. Off. |
| 2132364 | 11/1972 | France . |
| 2205503 | 5/1974 | France . |
| 2495137 | 4/1982 | France . |
| 53-2444 | 6/1976 | Japan . |
| 3141232 | 8/1978 | Japan . |
| 55-149223 | 11/1980 | Japan . |
| 60-55338 | 5/1981 | Japan . |
| 56-055338 | 5/1981 | Japan . |

*Primary Examiner*—Paul J. Killos
*Attorney, Agent, or Firm*—Cushman, Darby & Cushman

[57] ABSTRACT

A method for the preparation of a 2-hydroxymandelic acid of the formula

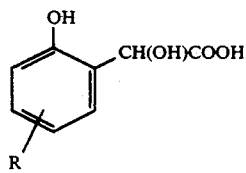

wherein R represents an alkyl radical containing from 7 to 12 carbon atoms which comprises reacting glyoxylic acid with a phenol of the formula:

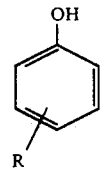

under acid conditions. Oxidation of the 2-hydroxymandelic acid to the corresponding 2-hydroxybenzaldehyde is also described.

4 Claims, No Drawings

PROCESS FOR MAKING 2-HYDROXYMANDELIC ACID AND 2-HYDROXYBENZALDEHYDES

This invention relates to a chemical process and more particularly to a method for the preparation of 2-hydroxymandelic acids and 2-hydroxybenzaldehydes.

The preparation of hydroxymandelic acids by reacting phenols with glyoxylic acid in an aqueous alkaline medium is well known, one such method having been described by Kalikar et al (J.Chem. Tech. Biotechnol 1986, 36 38-46). The hydroxymandelic acids are useful intermediates in the production of pharmaceuticals and dyes and may also be converted, by oxidation and decarboxylation, to the corresponding hydroxybenzaldehydes.

One especially useful hydroxybenzaldehyde is 5-nonylsalicylaldehyde, an intermediate in the manufacture of the metal extractant 5-nonylsalicylaldoxime, and whilst other methods for its preparation are known, many of these involve the use of heavy metal catalysts and it would be convenient if this aldehyde could be prepared from 4-nonylphenol by way of 2-hydroxy-5-nonylmandelic acid, a more environmentally friendly route. Unfortunately, attempts to react 4-nonylphenol with glyoxylic acid under the usual aqueous alkaline conditions have resulted only in recovery of the starting materials and the same negative result was obtained when using protic organic solvents such as methanol, aprotic solvents such as dimethylformamide or phase transfer catalysts.

It has now been found, however, that 2-hydroxy-5-nonylmandelic acid and related compounds can be obtained in good yield by reacting glyoxylic acid with the appropriate phenols under acid conditions.

Accordingly, the present invention provides a method for the preparation of a 2-hydroxymandelic acid of the formula:

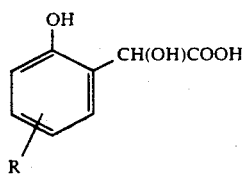
(1)

wherein R represents an alkyl radical containing from 7 to 12 carbon atoms which comprises reacting glyoxylic acid with a phenol of the formula:

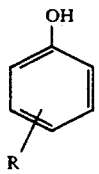
(2)

under acid conditions.

The acid conditions required by the method of the invention may be provided by the free glyoxylic acid but it is preferable to include an acid additional to glyoxylic acid in the reaction mixture. Suitable acids include inorganic acids such as boric acid or organic acids such as acetic acid or boric acid esters of the phenols employed in the reaction.

Accordingly, in a preferred embodiment, the invention provides a method for the preparation of a 2-hydroxymandelic acid of Formula 1 which comprises reacting glyoxylic acid with a boric acid ester of a phenol of Formula 2.

If desired, the boric acid ester may be formed in situ by heating a reaction mixture containing glyoxylic acid, boric acid and the phenol, the water of reaction being removed azeotropically. Higher yields may be obtained, however, by reacting the glyoxylic acid with a preformed boric acid ester which may be prepared by methods described in the prior art for phenol borates. Thus, for example, the phenol and boric acid in a molar ratio of from 3:1 to 0.5:1, typically from 3:1 to 1:1, especially about 1:1, may be heated together in a solvent which forms an azeotrope with the water evolved during the esterification reaction. Suitable solvents include aromatic hydrocarbons such as toluene.

The phenol/boric acid ester and the glyoxylic acid at a molar ratio of from 2:1 to 0.5:1, especially about 1:1, may be reacted together in any convenient manner. Preferably, the glyoxylic acid, available as a 50% aqueous solution, is added gradually to the phenol/boric acid ester in a solvent, for example toluene, capable of forming an azeotrope with water, the water being removed from the reaction zone as rapidly as possible. The product of this reaction is a boric acid ester/complex of the hydroxymandelic acid which may be decomposed by hydrolysis to liberate the required hydroxymandelic acid which may be separated from boric acid and isolated in conventional manner.

The 2-hydroxymandelic acids obtained by the method of the invention are valuable chemical intermediates. In particular, they may be converted to the corresponding 2-hydroxybenzaldehydes by oxidation and decarboxylation, suitable methods having been described in the prior art. Thus, oxidation and decarboxylation may be effected by heating the 2-hydroxymandelic acid with a suitable oxidant, for example ferric sulphate, alkaline copper oxide/ air, sodium periodate, tetrabutylammonium periodate or hydrogen peroxide. Particularly favourable oxidation conditions from the environmental viewpoint include the use of hydrogen peroxide in conjunction with a catalytic amount of a ferrous salt such as ferrous sulphate. More powerful oxidants capable of converting the aldehyde to carboxylic acid should be avoided. When the hydroxymandelic acid is obtained in the form of a boric acid ester complex, hydrolysis and oxidation may be effected simultaneously if desired.

Thus, in a further aspect, the invention provides a method for the preparation of a 2-hydroxybenzaldehyde of the formula:

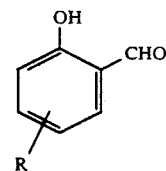
(3)

wherein R represents an alkyl radical containing from 7 to 12 carbon atoms which comprises reacting glyoxylic acid with a phenol of Formula 2 under acid conditions to form a 2-hydroxymandelic acid of Formula 1 and oxidising the 2-hydroxymandelic acid.

The method of the invention is particularly suitable for use in the preparation of 5-alkyl-2-hydroxymandelic acids, wherein the alkyl radical contains from 7 to 12 carbon atoms, and the derived 5-alkylsalicylaldehydes. Thus, 4-nonylphenol derived from phenol and propylene trimer may be reacted, especially in the form of its boric acid ester, with glyoxylic acid to prepare 2-hydroxy-5-nonylmandelic acid which may be converted to 5-nonylsalicylaldehyde, an intermediate in the manufacture of the metal extractant 5-nonylsalicylaldoxime.

The invention is illustrated but not limited by the following Examples.

EXAMPLE 1

| | | |
|---|---|---|
| 4-nonylphenol | 88 g | 0.40 mole |
| boric acid | 24 g | 0.40 mole |
| glyoxylic acid (50% aqueous) | 60 g | 0.40 mole |
| toluene | 400 ml | |
| ferric sulphate (42% aqueous) | 420 g | 0.44 mole |

The nonylphenol, boric acid and toluene were charged to a flask fitted with a mechanical stirrer and a Dean and Stark separator plus condenser. The mixture was heated in a mantle and refluxed for about 30 to 40 minutes at maximum rate until 7.5 ml water had collected and the boric acid had dissolved. The boil-up rate was 30–35 ml/minute measured by timing the collection rate of toluene in the collection leg of the Dean and Stark apparatus. The glyoxylic acid solution was then added in drops from a funnel over about 1 hour, maintaining a maximum reflux rate and reflux continued for 10 minutes after the last addition. A further 36.5 ml of water were collected.

The mixture was then cooled to about 50° C., 250 ml cold water added, the whole heated to reflux (870° C.) for about 10 minutes and then transferred to a preheated separating funnel. The phases separated cleanly in less than 5 minutes. On cooling, the aqueous phase deposited crystals of boric acid (12–13 g).

The organic phase was mixed vigorously with the aqueous ferric sulphate and heated to reflux (870° C.) over about 20 minutes. Decarboxylation was observed from about 50°–600° C. After a total oxidation time of 3 hours, the phases were separated in a preheated funnel. The aqueous phase on cooling yielded 85–90 g of pale green ferrous sulphate heptahydrate crystals. The organic phase was washed with 200 ml of 5% aqueous sulphuric acid to remove residual ferrous sulphate and then twice with 200 ml portions of hot water. The toluene was then removed on a rotary evaporator to yield 101–105 g of crude 5-nonylsalicylaldehyde as a light brown low viscosity oil.

| Typical analysis: by GLC the composition is typically as below: | |
|---|---|
| aldehyde | 61–64% |
| nonylphenol | 2–4% |
| low boilers | 1% |
| dialdehyde | <0.1% |
| yield | 63–65% of theory from glyoxylic acid. |

EXAMPLE 2

Crude 2-hydroxy-5-nonylmandelic acid (20 g), prepared as described in Example 1, and toluene (100 ml) were agitated for 3 hours at 40° C. with a solution of sodium periodate (17 g) in water (140 ml).

The organic phase was separated from the aqueous phase and the toluene was removed to give a crude product (15.5 g) found by GLC analysis to contain nonylphenol (31.7%) and 5-nonylsalicylaldehyde (24.6%).

EXAMPLE 3

Crude 2-hydroxy-5-mandelic acid (7.35 g), prepared as described in Example 1, toluene (54 ml), sodium hydroxide (1.36 g), cupric oxide (0.67 g) and water (50 ml) were heated to 90° C. and air was bubbled through (1 cm$^3$/sec) for 10 hours.

The mixture was cooled and acidified and the organic phase was separated from the aqueous phase. Removal of toluene from the organic phase gave a dark oil (5.13 g) containing 37.3% 5-nonylsalicylaldehyde by GLC.

EXAMPLE 4

A mixture of 4-nonylphenol (88 g), 50% aqueous glyoxylic acid (60 g) and boric acid (24 g) was slurried with toluene (400 ml) and then refluxed with azeotropic removal of water (until 37.2 ml removed).

The reaction mixture was washed twice with hot water to hydrolyse the boric acid ester and the resulting solution of 2-hydroxy-5-nonylmandelic acid was oxidised with ferric sulphate using the procedure described in Example 1. The final product contained 5-nonylsalicylaldehyde (56.7%) and nonylphenol (3.4%), the yield of aldehyde being 56% of theory.

EXAMPLE 5

| Materials | Mole Wt | Act. Wt (g) | 100% Wt (g) | G Moles | Mole Ratio |
|---|---|---|---|---|---|
| 4-Nonyl phenol | 220 | 22.0 | 22.0 | 0.1 | 1.0 |
| Boric acid | 62 | 6.2 | 6.2 | 0.1 | 1.0 |
| Glyoxylic acid (50%) | 74 | 14.8 | 7.4 | 0.1 | 1.0 |
| Ferric sulphate (42%) | 400 | 105.0 | 44.1 | 0.11 | 1.1 |
| Toluene (dry) | 92 | 65.0 | 65.0 | 0.71 | 7.1 |

The nonyl phenol, boric acid and toluene were charged to a flask. A nitrogen bleed was maintained over the liquid surface and the flask contents were heated to reflux (109° C.). Water generated by the condensation was azeotroped off via a Dean & Stark side arm (2.7 g collected). Glyoxylic acid solution was added dropwise to the flask over a period of 1.5 to 2.0 hours whilst removing the added water by azeotropic distillation. On completion of the addition, the reaction mass was maintained at reflux for a further 1 to 2 hours until no more water was collected (total water=8.5 g). HPLC analysis showed complete reaction of nonyl phenol.

The borate ester was then hydrolysed at reflux for 30 minutes with 62 g water to liberate the nonyl hydroxymandelic acid. The hot reaction mixture was transferred to a separating funnel and the lower aqueous phase (containing recovered boric acid) was separated off. The toluene layer was returned to the flask with the ferric sulphate solution and heated at reflux (870° C.) for 3 to 4 hours until the oxidation/decarboxylation was complete as judged by HPLC analysis.

A hot separation was carried out to remove the lower aqueous layer (containing ferrous sulphate). The toluene solution was washed with 5% sulphuric acid (52.5 g) and then with water (2×50 g) before finally stripping off the solvent on a rotary evaporator at 65° C./15 mm.Hg for 1.5 hours.

Weight of crude aldehyde=24.21 g
Strength (GC vs Int.Std)=50.9%
Yield based on nonyl phenol=49.7%

A series of experiments using the above procedure, where the ratio of nonyl phenol:boric acid was varied, gave the following results:

| Nonyl phenol | Boric Acid | Glyoxylic Acid | % Yield |
|---|---|---|---|
| 0.8 | 1 | 1 | 41.3 |
| 1 | 1 | 1 | 49.6 |
| 2 | 1 | 1 | 37.2 |
| 3 | 1 | 1 | 24.2 |
| 4 | 1 | 1 | 23.1 |

EXAMPLE 6

| Materials | Mole Wt | Act. Wt (g) | 100% Wt (g) | G Moles | Mole Ratio |
|---|---|---|---|---|---|
| 4-Nonyl phenol | 220 | 22.0 | 22.0 | 0.1 | 1.0 |
| Boric acid | 62 | 7.8 | 7.7 | 0.125 | 1.25 |
| Glyoxylic acid (50%) | 74 | 14.8 | 7.4 | 0.1 | 1.0 |
| Ferric sulphate (42%) | 400 | 105.0 | 44.1 | 0.11 | 1.1 |
| Toluene (dry) | 92 | 65.0 | 65.0 | 0.71 | 7.1 |

The procedure described in Example 5 was repeated except that after formation of the nonyl hydroxymandelic acid, the ferric sulphate solution was added directly to the toluene solution of borate ester and the mixture stirred at reflux to complete the hydrolysis and oxidation steps simultaneously. The product was isolated via the procedure in Example 5 to give a red brown viscous oil residue.

Weight of crude aldehyde=26.1 g
Strength (GC vs Int. Std.)=36.8%
Yield based on nonyl phenol=38.7%

EXAMPLE 7

| Materials | Mole Wt | Act. Wt (g) | 100% Wt (g) | G Moles | Mole Ratio |
|---|---|---|---|---|---|
| 4-Nonyl phenol | 220 | 22.0 | 22.0 | 0.1 | 1.0 |
| Glyoxylic acid (42%) | 74 | 14.8 | 7.4 | 0.1 | 1.0 |
| Glacial acetic acid | 60 | 26.2 | 26.2 | 0.44 | 4.4 |

The nonyl phenol and glyoxylic acid were charged to a flask containing the glacial acetic acid. The mixture was stirred and heated to reflux (106° C.) for a total of 7.0 hours. The reaction was monitored by HPLC and analysis showed that the formation of nonyl hydroxymandelic acid reached a maximum of about 50% after 4.5 hours with approximately 35% of the nonyl phenol remaining.

EXAMPLE 8

| Materials | Mole Wt | Act. Wt (g) | 100% Wt (g) | G Moles | Mole Ratio |
|---|---|---|---|---|---|
| 4-Nonyl phenol | 220 | 22.0 | 22.0 | 0.1 | 1.0 |
| Boric acid | 62 | 6.2 | 6.2 | 0.1 | 1.0 |
| Glyoxylic acid (50%) | 74 | 14.8 | 7.4 | 0.1 | 1.0 |
| Hydrogen peroxide (25%) | 34 | 27.2 | 6.8 | 0.2 | 2.0 |
| Toluene (dry) | 92 | 65.0 | 65.0 | 0.71 | 7.1 |

The nonyl phenol, boric acid and toluene were charged to a flask. A nitrogen bleed was maintained over the liquid surface and the flask contents were heated to reflux (109° C.). Water generated by the condensation was azeotroped off via a Dean & Stark side arm (2.4 g collected). The glyoxylic acid solution was added dropwise to the flask over a period of 1.5 to 2.0 hours whilst removing the water by azeotropic distillation. On completion of the addition, the reaction mass was maintained at reflux for a further 1 to 2 hours until no more water was collected (total water=10.5 g). HPLC analysis showed complete reaction of nonyl phenol.

The borate ester was then hydrolysed at reflux for 30 minutes with 62 g water to liberate the nonyl hydroxymandelic acid. The hot reaction mixture was transferred to a separating funnel and the lower aqueous phase (containing recovered boric acid) was separated off. The toluene layer was returned to the flask and heated to 75° C. Hydrogen peroxide solution was then added dropwise over a period of 12.0 hours. HPLC monitoring showed that the oxidation and decarboxylation was slow and came to a halt after 48.6% (HPLC Area %) aldehyde had been formed with 20.6% of the nonylhydroxymandelic acid remaining.

After a hot separation to remove the lower aqueous layer the toluene phase was washed with 5% sulphuric acid (52.5 g) and then with water (2×50 g) before finally stripping off the solvent on a rotary evaporator at 65° C./15 mm Hg for 1.5 hours to yield a dark brown viscous oil.

Weight of crude aldehyde=25.4 g
Strength (GC vs Int.Std.)=13.4%
Yield of product based on nonyl phenol=13.7%

EXAMPLE 9

| Materials | Mole Wt | Act. Wt (g) | 100% Wt (g) | G Moles | Mole Ratio |
|---|---|---|---|---|---|
| 4-Nonyl phenol | 220 | 22.0 | 22.0 | 0.1 | 1.0 |
| Boric acid | 62 | 6.2 | 6.2 | 0.1 | 1.0 |
| Glyoxylic acid (50%) | 74 | 14.8 | 7.4 | 0.1 | 1.0 |
| Hydrogen peroxide (25%) | 34 | 15.0 | 3.74 | 0.11 | 1.1 |
| Ferrous sulphate 7H$_2$O | 278 | 0.56 | 0.56 | 0.002 | 0.02 |
| Toluene (dry) | 92 | 65.0 | 65.0 | 0.71 | 7.1 |

The procedure described in Example 8 was repeated but, after hydrolysis to liberate the free nonyl hydroxymandelic acid, the aqueous layer was separated off and the toluene solution was charged to the flask with ferrous sulphate solution (0.56 g in 20 g water). The mixture was heated to 50°-55° C. and hydrogen peroxide solution added dropwise, to continually re-oxidise the ferrous ion, over a period of 3.0 hours. Stirring was continued for a further hour to complete the reaction (as judged by HPLC analysis) and then the aqueous layer was separated off. The toluene solution was washed with 10% sulphuric acid (50 g) and water (50 g) then finally vacuum stripped at 66° C./15 mm Hg for 1.5 hours.

Weight of crude product=25.9 g
Strength (GC vs Int.Std)=32.8%
Yield based on nonyl phenol=34.2%

We claim:
1. A method for the preparation of a 2-hydroxymandelic acid of the formula

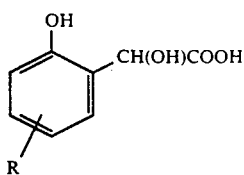

wherein R represents an alkyl radical containing from 7 to 12 carbon atoms which comprises reacting glyoxylic acid with a boric acid ester of a phenol of the formula:

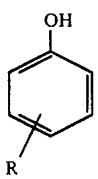

under acid conditions.

2. A method according to claim 1 wherein the phenol is 4-nonylphenol.

3. A method for preparation of a 2-hydroxybenzaldehyde of the formula wherein R represents an alkyl radical containing from 7 to 12 carbon atoms which comprises (a) reacting glyoxylic acid with a boric acid ester of a phenol of the formula:

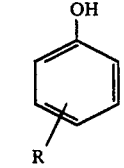

under acid conditions to form a boric acid ester of a 2-hydroxymandelic acid;

(b) decomposing the boric acid ester of the 2-hydroxymandelic acid, the (c) oxidising the 2-hydroxymandelic acid so obtained.

4. A method according to claim 3 wherein the phenol is 4-nonylphenol.

* * * * *